United States Patent [19]

Bergeron, Jr.

[11] Patent Number: 5,367,113
[45] Date of Patent: Nov. 22, 1994

[54] METHOD FOR SYNTHESIS OF DESFERRIOXAMINE B, ANALOGS AND HOMOLOGS THEREOF

[75] Inventor: Raymond J. Bergeron, Jr., Gainesville, Fla.

[73] Assignee: University of Florida Research Foundation, Inc., Alachua, Fla.

[21] Appl. No.: 80,184

[22] Filed: Jun. 23, 1993

Related U.S. Application Data

[62] Division of Ser. No. 784,949, Oct. 30, 1991, Pat. No. 5,254,724.

[51] Int. Cl.[5] .................................... C07C 259/06
[52] U.S. Cl. ......................... 562/623; 560/312; 558/390; 558/391; 558/394; 558/446; 558/451; 558/452; 524/153
[58] Field of Search .................... 560/312; 562/623

[56] References Cited

U.S. PATENT DOCUMENTS

| | | | |
|---|---|---|---|
| 3,247,197 | 4/1966 | Gaeumann et al. | 562/623 |
| 4,671,901 | 6/1987 | Green | 562/623 |
| 4,764,523 | 8/1988 | Heinrich | 514/18 |
| 4,940,811 | 7/1990 | Peter | 558/262 |
| 4,954,634 | 9/1990 | Heinrich et al. | 562/623 |
| 4,987,253 | 1/1991 | Bergeron | 562/623 |
| 4,999,445 | 3/1991 | White et al. | 556/138 |
| 5,011,976 | 4/1991 | Wuts | 560/159 |
| 5,089,644 | 2/1992 | Quay et al. | 556/40 |
| 5,185,368 | 2/1993 | Peter | 514/476 |

FOREIGN PATENT DOCUMENTS 9005716  5/1990  WIPO .................... 562/623

*Primary Examiner*—Marianne M. Cintins
*Assistant Examiner*—Keith MacMillan
*Attorney, Agent, or Firm*—Kerkam, Stowell, Kondracki & Clarke

[57] ABSTRACT

Synthesis of desferrioxamine B and analogs and homologs thereof beginning with O-protected, N-protected hydroxylamine, which is N-alkylated to produce a protected N-4-cyanoalkylhydroxylamine which is acylated with a suitable anhydride. The resulting half-acid amide is subjected to a series of high yield condensations and reductions which vide desferrioxamine B in high overall yield. Alternatively, polyether analogs of desferrioxamine B can be prepared by reacting an activated polyether with the O-protected, N-protected hydroxylamine and subjecting the resulting product to a series of similar steps.

6 Claims, 4 Drawing Sheets

1  Desferrioxamine B(DFO)

2  R = CH₃
3  R = CH₂O(CH₂)₂O(CH₂)₂OCH₃

FIG. 3 (con't.)

2  R=CH₃
3  R=CH₂O(CH₂)₂O(CH₂)₂OCH₃

METHOD FOR SYNTHESIS OF DESFERRIOXAMINE B, ANALOGS AND HOMOLOGS THEREOF

Support for the research leading to the present invention was provided by NIH Grant No. HL-42817.

RELATED APPLICATIONS

This is a division of application Ser. No. 07/784,949 filed Oct. 30, 1991 (now U.S. Pat. No. 5,254,724 issued Oct. 19, 1993.

This application contains subject matter related to that described and claimed in U.S. Pat. No. 4,987,253, the entire contents of which are incorporated herein by reference.

BACKGROUND OF THE INVENTION

1. Field of the Invention

The present invention relates to an improved method for the synthesis of desferrioxamine B and analogs and homologs thereof.

2. Description of the Prior Art

The microbial iron chelator, siderophore, desferrioxamine B [N′-[5-[[4-[[5-acetylhydroxyamino)pentyl]amino-1,4-dioxobutyl]hydroxyamino]pentyl]-N-(5-aminopentyl)-N-hydroxybutane diamide] was isolated from *Streptomyces pilosus* and characterized by Bickel ["Metabolic products of actinomycetes. Ferrioxamine B," *Helv. Chim. Acta.*, Vol. 43, pp. 2129–2138] in 1960. It is a linear trihydroxamate ligand which forms a very stable hexacoordinate, octahedral [Modell et al, "The Clinical Approach to Thalassaemia," Grune and Stratton, London, p. 217–241 (1984)] complex with re (III), $K_f = 1 \times 10^{30}$ $M^{-1}$. The ligand employs its three bidentate hydroxamate units in chelating metal ions.

Although desferrioxamine B will bind a number of different +3 cations, e.g., Al (III), Ga (III), Cr (III), it exhibits a high specificity for Fe (III), and is utilized by *Streptomyces pilosus* for the acquisition of iron from the environment. Because of the ligand's metal selectivity and low toxicity, it has been employed in the treatment of several iron overload diseases, e.g., thalassaemia ["Development of Iron Chelators for Clinical Use," Martell et al, eds., Elsevier, North Holland; New York (1981)]. However, desferrioxamine B does not offer a completely satisfactory solution to the iron overload problem. The drug is cleared by the kidneys and has a very short half-life in the body; thus, the patient must be maintained on constant infusion therapy. It is not orally effective. Because of these shortcomings, investigators have explored the potential of other ligands as therapeutic iron chelators. To date, these investigations have not included modification of the desferrioxamine molecule simply because of the lack of high yield of facile approaches to the synthesis of the molecule.

Desferrioxamine B was first synthesized in 1962 by Prelog et al ["Metabolic products of actinomycetes. Synthesis of Ferrioxamines B and D," *Helv. Chim. Acta.*, Vol. 45, pp. 631–637 (1962)]. However, because of the number of steps in the synthesis and the low yield of the sequence, the method does not enable the production of large quantities of the chelator or its analogs. A retro-synthetic analysis of the ligand reveals that the desferrioxamine molecule is made up of two fundamental units: 1-amino-5-(N-hydroxyamino)pentane and succinic acid. The key to its synthesis is the production of this amino-hydroxyaminopentane unit and its condensation with succinic acid. Prolog approached this problem beginning with the starting material 1-amino-5-nitropentane, an amine which was accessible in only 46% yield [Bickel et al, "Metabolic products of actinomycetes. Isolation and synthesis of 1-amino-5-(hydroxyamino)pentane, an essential hydrolysis product of ferrioxamine and ferrimycin," *Helv. Chim. Acta.*, Vol. 43, pp. 901–904 (1960)]. This compound was next N-carbobenzoxylated and the terminal nitro group reduced to the corresponding hydroxyamino group. This key intermediate was condensed with succinic acid followed by a series of other dicyclohexylcarbodiimide catalyzed acylations along with several reductions to produce desferrioxamine B. The overall yield of this eleven step sequence was 6%.

Bergeron et al ["An Efficient Total Synthesis of Desferrioxamine B," *J. Org. Chem.*, Vol. 53, pp. 3131–3134 (1988)] reported a total synthesis of desferrioxamine B (DFO) in which the construction moved from the N-acetyl to the primary amine end of the molecule.

It is an object of the present invention to provide novel, improved, high yield methods for the production of desferrioxamine B and homologs and analogs thereof, which proceeds in the opposite direction from that of Bergeron et al, supra, and avoids some of the problems associated with the reduction steps involved therein, is of high overall yield and begins with easily accessible starting materials.

SUMMARY OF THE INVENTION

The above and other objects are realized by the present invention, one embodiment of which comprises a method for synthesizing desferrioxamine B or a homolog or analog thereof having the formula:

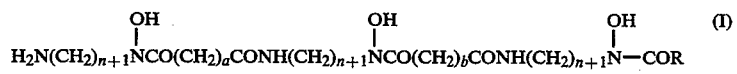

wherein:

each n may be the same or different and is an integer from 1 to 10;

a and b may be the same or different and are integers from 1 to 6; and

R is an alkyl group having from 1 to 10 carbon atoms or an aryl group, comprising:

(a) cleaving Q from a compound having the formula:

wherein

Z is a hydroxyl protecting group and

Q is an amino protecting group, to produce a protected hydroxylamine having the formula:

(b) condensing hydroxylamine (5) with an anhydride having the formula:

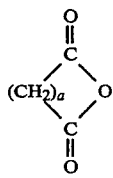

wherein a is an integer from 1 to 6 to produce a compound having the formula:

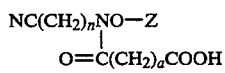

(6)

wherein n is an integer from 1 to 10, (c) reducing compound (4) to produce an amine having the formula:

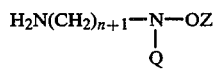

(7)

(d) condensing the carboxylic acid (6) with the amine (7) to produce a nitrile having the formula:

$$NC(CH_2)_n-\underset{OZ}{N}-CO(CH_2)_aCO-NH(CH_2)_{n+1}-\underset{Q}{N}-OZ \quad (8)$$

and cleaving Q therefrom to produce a protected hydroxylamine having the formula:

$$NC(CH_2)_n-\underset{OZ}{N}-CO(CH_2)_aCO-NH(CH_2)_{n+1}-NH-OZ \quad (9)$$

(e) reacting the protected hydroxylamine (9) with an anhydride having the formula:

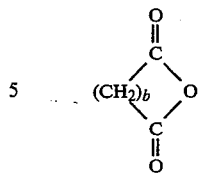

wherein b is an integer from 1 to 6 to produce a compound having the formula:

$$NC(CH_2)_n-\underset{OZ}{N}-CO(CH_2)_aCO-NH(CH_2)_{n+1}-\underset{OZ}{N}-CO(CH_2)_bCOOH \quad (10)$$

(f) reacting compound (10) with compound (7) to produce a nitrile having the formula:

$$NC(CH_2)_n-\underset{OZ}{N}-CO(CH_2)_aCO-NH(CH_2)_{n+1}-\underset{OZ}{N}-CO(CH_2)_bCONH(CH_2)_{n+1}-\underset{Q}{N}-Q \quad (11)$$

(g) cleaving Q therefrom to produce the protected hydroxylamine followed by acylation with any acylating agent RCOX wherein R is any alkyl group, straight or branched chain, with 1 to 10 carbon atoms or any hydrocathyl aryl group, and the leaving group X is any halide or other group which renders RCOX sufficiently active to acylate (11) to produce a compound having the formula:

$$NC(CH_2)_n-\underset{OZ}{N}-CO(CH_2)_aCONH(CH_2)_{n+1}-\underset{OZ}{N}-CO(CH_2)_bCONH(CH_2)_{n+1}-\underset{OZ}{N}-COR \quad (12)$$

and (h) reducing said compound (12) to produce said compound of formula (I).

A further embodiment of the invention is a synthesis of a polyether analog of DFO or a homolog or analog thereof having the formula:

$$R_1O(CH_2)_m-O-(CH_2)_m-O-(CH_2)_mN-CO(CH_2)_aCONH(CH_2)_n-\underset{OH}{\overset{OH}{N}}- \quad (II)$$

$$CO(CH_2)_bCONH-(CH_2)_n-\underset{}{\overset{OH}{N}}-CO(CH_2)_{m-1}O(CH_2)_mO(CH_2)_m-OR_2$$

wherein each n may be the same or different and is an integer from 1 to 10,
a is an integer from 1 to 6,
b is an integer from 1 to 6,
m is an integer from 2 to 6,
$R_1$ and $R_2$ may be the same or different and are alkyl, straight or branched chain, having 1-10 carbon atoms, comprising:

(a) reacting a compound of the formula:

$$R_1O(CH_2)_mO(CH_2)_mO(CH_2)_mOACT \quad (13)$$

wherein ACT is an alcohol activating group with a compound of the formula:

$$Q-NH-OZ$$

wherein
Q is an amino protecting group and
Z is a hydroxyl protecting group,
to produce a compound of the formula:

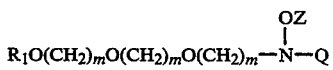  (14)

and cleaving Q to produce a compound of the formula:

  (15)

(b) reacting compound (15) with an anhydride of the formula:

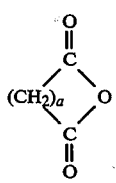

to produce a compound of the formula:

$R_1O(CH_2)_mO(CH_2)_mO(CH_2)_m\text{—}N\text{—}CO(CH_2)_a COOH$  (16)
(with OZ on N)

$H_2N(CH_2)_n\overset{OZ}{\underset{|}{N}}\text{—}Q$  (7)

to produce a compound of the formula:

  (17)

and cleaving Q therefrom to produce a compound of the formula:

  (18)

(d) reacting compound (18) with an anhydride of the formula:

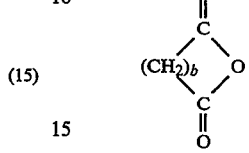

to produce a compound of the formula:

  (19)

(e) reacting compound (19) with compound (7) to produce a compound of the formula:

  (20)

and cleaving Q therefrom to produce a compound of the formula:

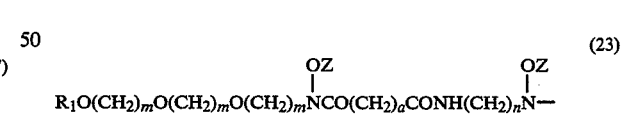  (21)

(f) reacting compound (21) with a compound of the formula:

$R_2O(CH_2)_mO(CH_2)_mO(CH_2)_{m-1}COX$  (22)

wherein X is Cl, Br, I, F or any leaving group which renders the compound sufficiently active to acylate (21), and
$R_2$ is alkyl, straight or branched chain, having 1–10 carbon atoms, to produce a compound of the formula:

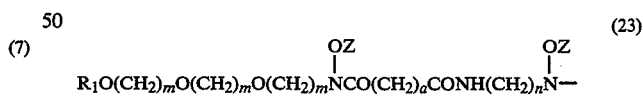  (23)
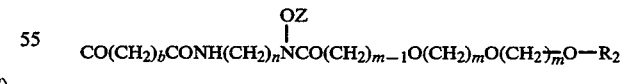

and
(g) reducing said compound (23) to produce said compound of formula (II).

Yet another embodiment of the invention relates to a synthesis of a polyether analog of DFO or a homolog thereof having the formula:

  (III)

wherein m is an integer from 2 to 6,
each n may be the same or different and is an integer from 1 to 10, a is an integer from 1 to 6, b is an integer from 1 to 6, $R_1$ is alkyl, straight or branched chain, having 1-10 carbon atoms, and
$R_3$ is alkyl, straight or branched chain, having 1-14 carbon atoms or any hydrocarbyl aryl group, comprising:

(a) reacting a compound of the formula:

$$R_1O(CH_2)_mO(CH_2)_mO(CH_2)_mOACT \quad (1)$$

wherein ACT is an alcohol activating group, with a compound of the formula:

$$Q-NEOZ$$

wherein
Q is an amino protecting group and
Z is a hydroxyl protecting group,
to produce a compound of the formula:

$$R_1O(CH_2)_mO(CH_2)_mO(CH_2)_m\overset{OZ}{\underset{|}{N}}-Q \quad (14)$$

and cleaving Q therefrom to produce a compound of the formula:

$$R_1O(CH_2)_mO(CH_2)_mO(CH_2)_m\overset{OZ}{\underset{|}{N}}H \quad (15)$$

(b) reacting compound (15) with an anhydride of the formula:

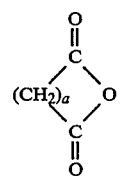

to produce a compound of the formula:

$$R_1O(CH_2)_mO(CH_2)_mO(CH_2)_m\overset{OZ}{\underset{|}{N}}CO(CH_2)_aCOOH \quad (16)$$

(c) reacting compound (16) with a compound of the formula:

$$H_2N(CH_2)_n\overset{OZ}{\underset{|}{N}}-Q \quad (7)$$

to produce a compound of the formula:

$$R_1O(CH_2)_mO(CH_2)_mO(CH_2)_m\overset{OZ}{\underset{|}{N}}CO(CH_2)_aCONH(CH_2)_n-\overset{OZ}{\underset{|}{N}}-Q \quad (17)$$

and cleaving Q therefrom to produce a compound of the formula:

$$R_1O(CH_2)_mO(CH_2)_mO(CH_2)_m\overset{OZ}{\underset{|}{N}}CO(CH_2)_aCONH(CH_2)_n-\overset{OZ}{\underset{|}{N}}-H \quad (18)$$

(d) reacting compound (18) with an anhydride of the formula:

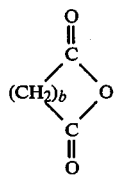

to produce a compound of the formula:

$$R_1O(CH_2)_mO(CH_2)_mO(CH_2)_m\overset{OZ}{\underset{|}{N}}CO(CH_2)_aCONH(CH_2)_n\overset{OZ}{\underset{|}{N}}CO(CH_2)_bCOOH \quad (19)$$

(e) reacting compound (19) with compound (7) to produce a compound of the formula:

$$R_1O(CH_2)_mO(CH_2)_mO(CH_2)_m\overset{OZ}{\underset{|}{N}}CO(CH_2)_aCONH(CH_2)_n\overset{OZ}{\underset{|}{N}}CO(CH_2)_bCONH(CH_2)_n-\overset{OZ}{\underset{|}{N}}-Q \quad (20)$$

and cleaving Q therefrom to produce a compound of the formula:

$$R_1O(CH_2)_mO(CH_2)_mO(CH_2)_m\overset{OZ}{\underset{|}{N}}CO(CH_2)_aCONH(CH_2)_n\overset{OZ}{\underset{|}{N}}CO(CH_2)_bCONH(CH_2)_n-\overset{OZ}{\underset{|}{N}}-H \quad (21)$$

(f) reacting compound (21) with an anhydride of the formula:

$$(R_3-CO)_2O$$

or an activated ester or acyl halide of the formula:

$$R_3COX$$

wherein
$R_3$ is as defined above and

X is Cl, Br, F, I or any leaving group sufficiently active to acylate (21),
to produce a compound of the formula:

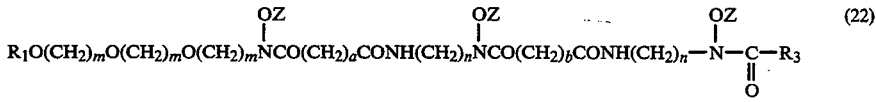

and
(g) reducing said compound (22) to produce said compound (III).

A further embodiment of the invention comprises the compounds of formulae (II) and (III) described above.

DETAILED DESCRIPTION OF THE INVENTION

Microorganisms produce a group of low molecular weight chelators, siderophores [Bergeton, "Synthesis and Solution Structures of Microbial Siderophores," Chem. Rev., Vol. 84, pp. 587–602 (1984); Tait, "The Identification and Biosynthesis of Siderochromes Formed by Micrococcus denitrificans, Biochem. J., Vol. 146, pp. 191–204 (1975); Griffiths et al, "Vibriobactin, a Siderophore from Vibrio cholerae," J. Biol. Chem., Vol. 259, pp. 383–385 (1984); Aksoy et al, "Hypertransfusion and Iron Chelation in Thalassaemia," p. 80, Hans Huber Publishers, Berne (1985); and Bickel et al, "Metabolic products of actinomycetes. Ferrioxamine B," Helv. Chim. Acta., Vol. 43, pp. 2129–2138 (1960)] for the purpose of acquiring iron. The metal exists in the biosphere largely in the insoluble ferric state and would be otherwise inaccessible to bacteria without such ligands. Although a large number of siderophores have been identified, they fall largely into two structural classes: the catecholamides and the hydroxamates [Bergeton, supra]. Many of the ligands of both structural types contain polyamine backbones. While the hexacoordinate catecholamides parabactin [Tait, supra] and vibriobactin [Griffiths et al, supra] are predicated on the substituted triamines spermidine and norspermidine, respectively, the hydroxamates are frequently derived from the diamines, putrescine or cadaverine, or from their biochemical precursors, ornithine or lysine [Bergeron, supra]. For example, the siderophores isolated from Streptomyces pilosus, desferrioxamines A-I, consist of a group of hydroxamates with either repeating putrescine or cadaverine units in their backbones [Aksoy et al, supra]. The most well known of these chelators, desferrioxamine B (DFO) [Bickel et al, Helv. Chim, Acta., Vol. 43, pp. 2129–2138, supra], is a linear trihydroxamate ligand which forms a very stable hexacoordinate, octahedral complex [Modell et al, supra] with iron (III), $K_f = 1 \times 10^{30} M^{-1}$. Although DFO binds a number of different +3 cations, e.g., Al (III), Ga (III), Cr (III), it exhibits a high specificity for iron (III). It is not too surprising then that the mesylate salt of desferrioxamine, Desferal, has been employed in the treatment of several iron overload diseases such as thalassemia [Anderson, "Inorganic Chemistry in Biology and Medicine," Chapter 15, American Chemical Society, Washington, D.C. (1973); and Fisher et al, "Development of an Intravenous Desferrioxamine Mesylate Treatment Protocol for Swine: Monitoring of Desferrioxamine and Metabolites for High-Performance Liquid Chromatography," Pharmacology, Vol. 41, pp. 263–271 (1990)]. However, the fact that patients must be continuously infused because of the short half-life of the drug in the body has compelled investigators to continue the search for better therapeutic iron chelators.

Figure 1:
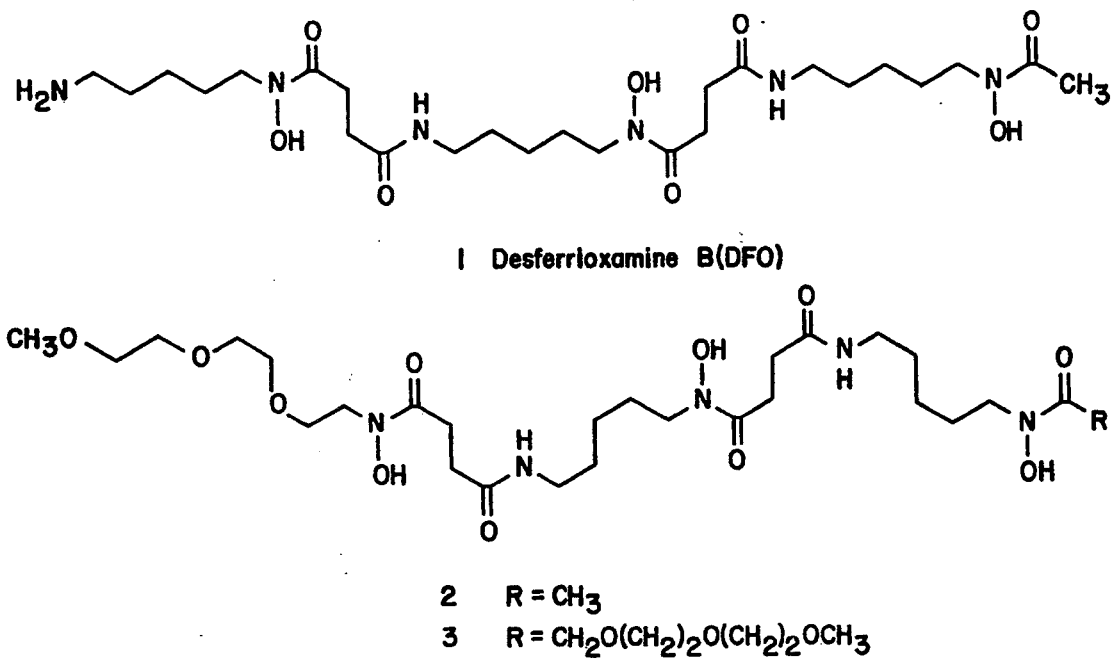
FIG. 1 depicts the structural formulae of DFO (1) and two of its analogs (2) and (3) produced according to the methods of the invention.

The present invention provides a new and versatile route to DFO (1) (FIG. 1), predicated on employing as a starting material triprotected N-hydroxycadaverine reagent [Bergeron et al, "The Total Synthesis of Bisucaberin, Tetrahedron, Vol. 45, pp. 4939–4944 (1989)]. In the earlier reported synthesis of DFO [Bergeron et al, J. Org. Chem., supra] and U.S. Pat. No. 4,987,253, the construction moved from the N-acetyl to the primary amine end of the molecule. The method of the present invention proceeds in the opposite direction, avoids some of the problems associated with reduction steps, is of high overall yield and begins with easily accessible starting materials. The methodology was also utilized to access several desferrioxamine analogs which showed promising activity in terms of their ability to remove iron from rats. These derivatives include polyethercontaining ligands (2) and (3) (FIG. 1), which were designed to be lipophilic. In both instances, this change in solubility properties rendered the drug more effective than desferrioxamine at removing iron in the rodent model.

Figure 2:
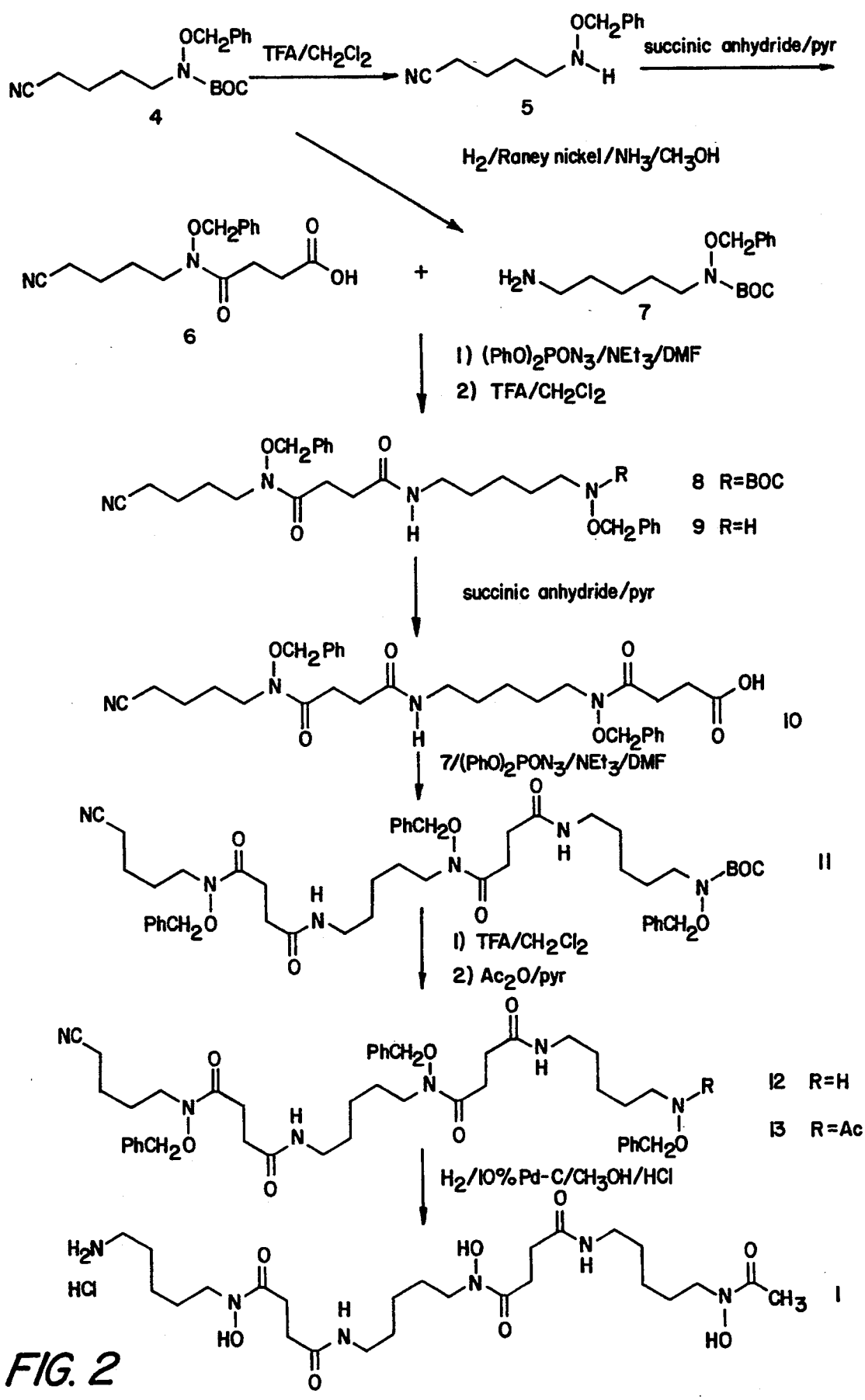
FIG. 2 depicts a typical reaction scheme for a method of the invention for producing DFO.

The new route (FIG. 2) begins with the generation and selective diprotection of triprotected N-hydroxycadaverine (4), also used to prepare bisucaberin [Bergeron et al, Tetrahedron (1989), supra]. The backbone of DFO was constructed by a series of acylations such that the acetyl function was attached at the end of the synthesis. In the key synthon (4), the primary amine was masked as a nitrile, while the hydroxylamine was, e.g., N-(tert-butoxycarbonyl), and, e.g., O-benzyl diprotected. It will be understood by those skilled in the art that any of the well known OH and amine protective groups could be employed in the practice of the invention. The synthesis of reagent (4) begins with the conversion of O-benzylhydroxylamine hydrochloride to its N-(tert-butoxycarbonyl) derivative [Ramasamy et al, "N-Methylation of O-Benzyl-N$^\alpha$-(Alkoxycarbonyl)-$\alpha$-Amino Acid Hydroxamate Derivatives," J. Org. Chem., Vol. 46, pp. 5438–5441 (1981)] which is crystalline, stable and available in a single step from commercial reagents. N-(tert-Butoxycarbonyl)-O-benzylhydroxylamine was N-alkylated with 5-chlorovaleronitrile (NaI, DMF, NaI) to give O-benzyl-N-(tert-butoxycarbonyl)-N-(4-cyanobutyl)-hydroxylamine (4). The O-benzyl protecting group in (4) was left intact until hydrogenation, e.g., (Pd-C) to the final product (1). N-(tert-Butoxycarbonyl)-O-benzylhydroxylamine can also be N-alkylated with commercially available ω-chloroalkanenitriles to either shorten or lengthen the N-hydroxydiamine chain. Thus, the length of DFO can be varied through this flexible synthetic strategy. In contrast, the previous synthesis [Bergeton et al, J. Org. Chem., supra] of DFO begins with 4-cyanobutanal, which is made by a tedious method and is somewhat unstable. Moreover, if one wanted to vary the length of the N-hydroxydiamine chains of DFO, a new and reactive cyano aldehyde would be required.

Brief exposure of N-(tert-butoxycarbonyl)nitrile (4) to trifluoroacetic acid (TFA) resulted in collapse to carbon dioxide, isobutylene and O-benzyl-N-(4-cyanobutyl)hydroxylamine (5), thus freeing up the hydroxylamine nitrogen. Alternatively, the nitrile in (4) was selectively hydrogenated in the presence of the benzyl group to generate primary amine (7) with, e.g., W-2 grade Raney nickel in methanolic ammonia. This high yield reaction required no pre-washing of the catalyst. In the previous route [Bergeton et al, J. Org. Chem., supra], even with such pretreatment of the nickel catalyst, hydrogenation of nitriles which contained the base sensitive succinate unit occurred in variable yields. Benzyloxyamine (5) was acylated with succinic anhydride in hot pyridine to give half acid nitrile (6) [Bergeron et al, J. Org. Chem., supra]. If succinic anhydride were replaced with glutaric anhydride in FIG. 2, homologs of DFO could easily be generated. Coupling of acid (6) with primary amine (7) was carried out with diphenylphosphoryl azide, the Yamada reagent [Shioiri et al, "Diphenylphosphoryl Azide, A New Convenient Reagent for a Modified Curtius Reaction and for the Peptide Synthesis," J. Am. Chem. Soc., Vol. 94, pp. 6203–6205 (1972)] (NEt3/DMF) to afford masked tetracoordinate ligand (8). The phosphoryl azide provided to be a superior amide coupling agent to dicyclohexylcarbodiimide (DCC), which had been employed in the previous synthesis [Bergeron et al, J. Org. Chem., supra]. The yields were consistently higher and the phosphorus containing by-product can be washed away from the product, in contrast to dicyclohexylurea (DCU). The elaboration was repeated: (tert-butoxycarbonyl)nitrile (8) was treated with TFA to give benzyloxyamine (9). Acylation of (9) with succinic anhydride as before generated nitrile acid (10) which was, in turn, reacted with diprotected cadaverine (7) using the Yamada reagent to give (tertbutoxycarbonyl)nitrile (11), a versatile precursor to hexacoordinate chelators. In addition to providing DFO (1) in three transformations, nitrile (11) permitted the chemical modification of DFO at both the acyl and the amino termini for the purpose of determining the structure-activity relationship. The terminal tert-butoxycarbonyl protecting group of (11) can be replaced with any acyl functionality that one chooses. In the previous method [Bergeton et al, J. Org. Chem., supra], the acetyl group was attached early in the sequence, thus restricting the versatility of that synthesis. Alternatively, the cyano group in (11) could be selectively hydrogenated using pre-washed Raney nickel in methanolic ammonia, and then the amino end of DFO could be modified by using an active ester or other electrophile. In order to complete the synthesis of DFO (1), acid-promoted deprotection of (11) to benzyloxyamine (12) was followed by acylation with acetic anhydride in pyridine to give masked DFO (13). Simultaneous catalytic reduction of the nitrile and removal of the O-benzyl protecting groups as before [Bergeton et al, J. Org. Chem., supra] generated the natural product DFO (1).

Figure 3:
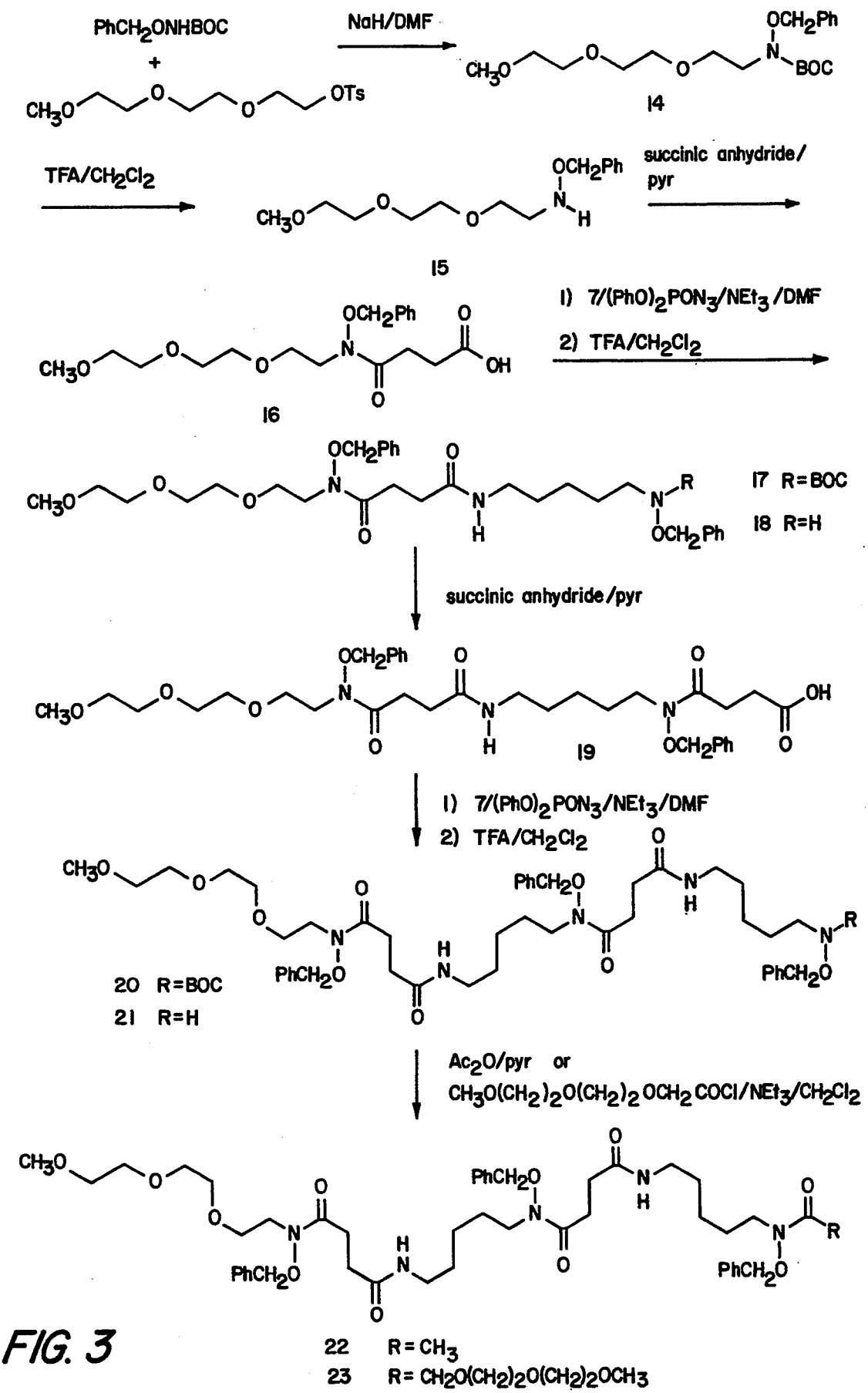
FIG. 3 depicts a typical reaction scheme for a method of the invention for producing analogs of DFO.

The short half-life of DFO in the body and the fact that patients must be continuously infused led investigators to prepare and test analogs of DFO as potential therapeutic iron chelators. In the search for useful analogs of DFO, it was previously determined that replacement of the terminal 5-aminopentyl unit of desferrioxamine B with a heptyl group rendered the molecule very insoluble in a variety of different vehicles [Bergeton et al, J. Org. Chem., supra]. Therefore, polyether analogs of DFO, chelators (2) and (3) in FIG. 1, were prepared in order to enhance the chelator's lipophilicity as well as to maintain some degree of aqueous solubility. Specifically, in DFO polyether analogue 2, the charged 5-aminopentyl chain was replaced with a neutral triether chain and in bis(polyether) (3), the acetyl of DFO was substituted as well by a triether acyl group. The syntheses of chelators (2) and (3) utilized the new DFO synthetic methodology (FIG. 2) and are illustrated in FIG. 3.

The monomethyl ether of triethylene glycol was converted to its tosylate [Schultz et al, "12-, 15- and 18-Membered-Ring Nitrogen-Pivot Lariat Ethers: Syntheses, Properties and Sodium and Ammonium Cation Binding Properties," J. Am. Chem. Soc., Vol. 107, pp. 6659–6668 (1985)] which was used to alkylate N-(tert-butoxycarbonyl)-O-benzylhydroxylamine (NaH/DMF), resulting in polyether (14). By contrast, the methodology of the old route [Bergeton et al, J. Org. Chem., supra] required conversion of the alcohol to the corresponding reactive aldehyde instead of the tosylate. The alkylated product (14) was elaborated in the manner of the DFO synthesis (FIG. 2): stirring it with TFA in $CH_2Cl_2$ gave (15) which was then acylated with succinic anhydride to afford carboxylic acid (16). Coupling of (16) and primary amine (7) was carried out in high yield with the phosphoryl azide reagent to tetracoordinate equivalent (17). The protected hexacoordinate reagent (20) was obtained in high overall yield from (17) by repeating the same three conversions. Acid cleavage of the tert-butoxycarbonyl group in (20) furnished benzyloxyamine (21), which can be reacted with a wide range of activated esters to give any hexacoordinate polyether chelator desired after catalytic debenzylationamine (21) was acylated with acetic anhydride (pyr/RT) to produce (22) or with 3,6,9-trioxadecanoyl chloride [Heimann et al, "Hydrophilic lipids," Liebigs Ann. Chem., pp. 858–862 (1980)] ($NEt_3/CH_2Cl_2$) to afford (23). Catalytic debenzylation of (22) and (23) gave hexacoordinate ligands (2) and (3), respectively. Both of these chelators are soluble in water and chloroform and thus possess enhanced lipophilicity and the aqueous solubility of DFO.

Acetyl triether (2) and bis(triether) (3) were evaluated in a non-iron overloaded bile duct-cannulated rat model [Bergeron et al, "A Comparative Evaluation of Iron Clearance Models," Ann. N. Y. Acad. Sci., Vol. 612, pp. 378–393 (1990); and Bergeron et al, "Evaluation of Desferrithiocin and its Synthesis Analogues As Orally Effective Iron Chelators," *J. Med. Chem.*, Vol. 34, pp. 2072–2078 (1991)]. Studies involved both subcutaneous and oral administration of the drugs in Cremophor RH-40/water (40/60 V/V). The chelator-promoted iron excretion was monitored in both the bile and the urine, and the results were compared to a standard desferrioxamine dose given either orally (p.o.) or subcutaneously (s.c.) also given in Cremophor RH-40/water. The rats were fasted for 48 hours prior to drug administration and throughout the course of the experiment. The iron excretion data for the drugs evaluated in this study are reported in Tables 1 and 2 with comparative data for p.o. and s.c. desferrioxamine. The data are presented in total "induced" iron excreted over 24 hours, per kilogram of rat weight. The values are derived from the difference between the total iron excreted in test animals vs. control animals on a per weight basis. This measurement does not speak to potential enterohepatic absorption where the iron chelator complex may be reabsorbed and thus decrease the amount of iron cleared, but only to the ability of the drug to access iron stores.

The data set forth herein also demonstrates the efficacy of the compounds of formulae (II) and (III) as iron chelators.

ance was unremarkable in all of the animals, with iron excretion only slightly higher than that observed in the control (Cremophor-water) animals.

Figure 5:
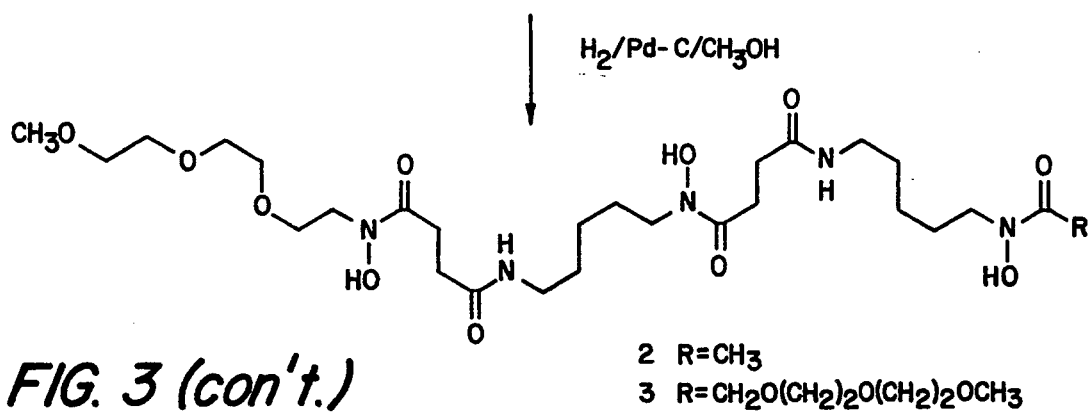
FIG. 5 is a graphical depiction of the cumulative biliary iron clearance induced by analogs (2) and (3) compared with that of DFO (1) when administered subcutaneously.
Figure 5:
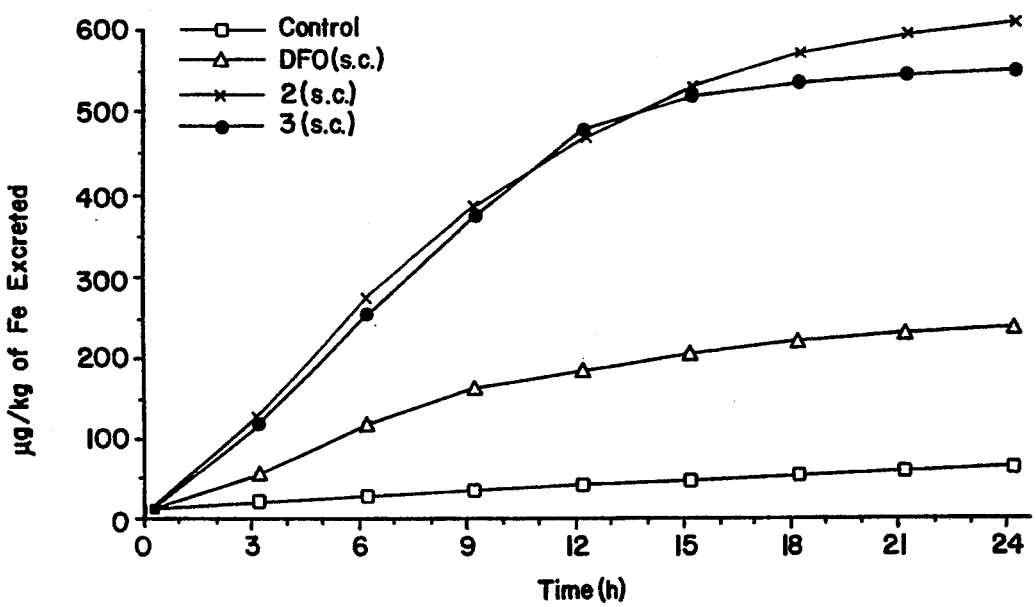

When either ligand (2) or (3) was administered subcutaneously at 150 $\mu$mol/kg, far more iron was excreted than with DFO administered subcutaneously at the same dose in $\mu$mol/kg. Analog (2) was nearly three times as effective as DFO in promoting iron clearance, while analog (3) was 2.5 times as effective as DFO (FIG. 5).

Figure 6:
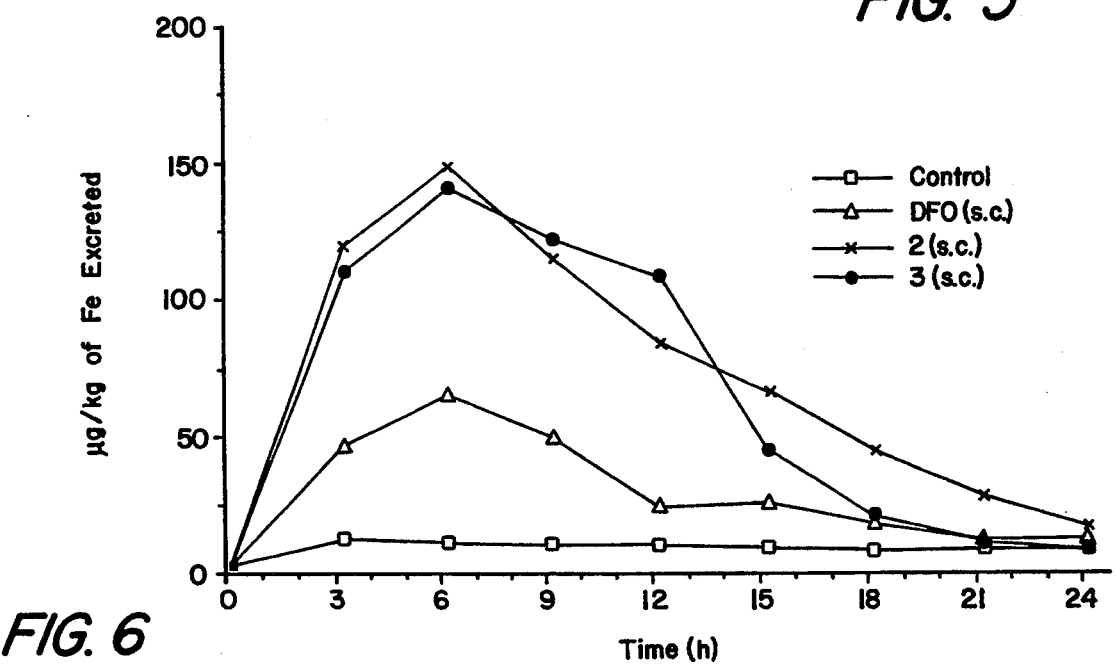
FIG. 6 is a graphical depiction of the ferrokinetic clearance properties of analogs (2) and (3) compared with that of DFO (1) when administered subcutaneously.

Biliary iron clearance induced by a single subcutaneous dose of DFO was back to baseline clearance in 15 hours, with its maximum output at 6 hours. Chelators (2) and (3) given subcutaneously had similar spikes at 6 hours, but the iron clearance time was protracted: levels returned to baseline only after 27 hours for (2) and 21 hours for (3) (FIG. 6).

The invention is illustrated by the following non-limiting examples.

EXAMPLE 1

Bile Duct Cannulation

Male Sprague-Dawley rats averaging 400 grams were housed in Nalgene plastic metabolic cages during the experimental period and were given free access to water. The animals were anesthetized using sodium pentobarbital (50 mg/kg) given intraperitoneally (j.p.). The bile duct was cannulated using 22-gauge polyethylene tubing (Intramedic) about 1 cm from the duodenum. The cannula was inserted about 2 cm into the duct and

TABLE 1

COMPARISON OF TOTAL IRON OUTPUT INDUCED BY DFO (P.O.) AND ANALOGS (2) AND (3) (P.O.) OVER 24 HOURS, PER KILOGRAM OF RAT WEIGHT

| | Control | DFO (p.o.) | 2 (p.o.) | 3 (p.o.) |
|---|---|---|---|---|
| Bile (h) | | | | |
| 3 | 9.1 ($\pm$1.2) | 14.7 ($\pm$5.2) | 20.2 ($\pm$3.5) | 16.3 ($\pm$6.5) |
| 6 | 17.4 ($\pm$2.3) | 43.9 ($\pm$13.7) | 42.8 ($\pm$7.7) | 31.7 ($\pm$7.8) |
| 9 | 24.7 ($\pm$2.3) | 76.8 ($\pm$19.6) | 56.8 ($\pm$8.1) | 42.5 ($\pm$8.0) |
| 12 | 31.6 ($\pm$2.9) | 97.1 ($\pm$21.9) | 67.5 ($\pm$8.5) | 59.7 ($\pm$14.6) |
| 15 | 37.1 ($\pm$3.0) | 110.8 ($\pm$22.9) | 76.5 ($\pm$8.6) | 67.9 ($\pm$14.8) |
| 18 | 42.4 ($\pm$3.0) | 119.8 ($\pm$22.9) | 83.8 ($\pm$8.8) | 74.6 ($\pm$14.9) |
| 21 | 47.9 ($\pm$3.4) | 128.7 ($\pm$23.0) | 89.0 ($\pm$8.8) | 81.3 ($\pm$15.2) |
| 24 | 53.5 ($\pm$3.6) | 135.0 ($\pm$23.1) | 93.7 ($\pm$8.8) | 86.6 ($\pm$15.4) |
| Urine (h) | | | | |
| 24 | 11.7 ($\pm$1.3) | 16.5 ($\pm$1.0) | 15.0 ($\pm$3.2) | 13.3 ($\pm$6.6) |
| Total | 65.2 ($\pm$3.8) | 277.6 ($\pm$34.2) | 667.9 ($\pm$47.0) | 585.0 ($\pm$39.6) |
| Induced Iron (Treated-Control) | — | 86.3 | 43.5 | 34.6 |

TABLE 2

COMPARISON OF TOTAL IRON OUTPUT INDUCED BY DFO (S.C.) AND ANALOGS (2) AND (3) (S.C.) OVER 24 HOURS, PER KILOGRAM OF RAT WEIGHT

| | Control | DFO (p.o.) | 2 (p.o.) | 3 (p.o.) |
|---|---|---|---|---|
| Bile (h) | | | | |
| 3 | 9.1 ($\pm$1.2) | 43.6 ($\pm$18.2) | 117.3 ($\pm$26.7) | 106.9 ($\pm$6.8) |
| 6 | 17.4 ($\pm$2.3) | 105.9 ($\pm$21.2) | 262.5 ($\pm$27.9) | 244.4 ($\pm$11.4) |
| 9 | 24.7 ($\pm$2.3) | 152.8 ($\pm$22.3) | 374.6 ($\pm$28.7) | 362.6 ($\pm$21.1) |
| 12 | 31.6 ($\pm$2.9) | 173.9 ($\pm$22.9) | 456.1 ($\pm$32.3) | 467.7 ($\pm$33.7) |
| 15 | 37.1 ($\pm$3.0) | 196.2 ($\pm$25.9) | 519.6 ($\pm$39.2) | 509.1 ($\pm$38.5) |
| 18 | 42.4 ($\pm$3.0) | 210.7 ($\pm$27.8) | 561.2 ($\pm$42.4) | 526.2 ($\pm$39.2) |
| 21 | 47.9 ($\pm$3.4) | 219.8 ($\pm$27.8) | 585.9 ($\pm$43.4) | 534.2 ($\pm$39.3) |
| 24 | 53.5 ($\pm$3.6) | 228.4 ($\pm$27.9) | 599.6 ($\pm$43.7) | 539.7 ($\pm$39.3) |
| Urine (h) | | | | |
| 24 | 11.7 ($\pm$1.3) | 49.2 ($\pm$19.8) | 68.4 ($\pm$17.5) | 45.3 ($\pm$4.8) |
| Total | 65.2 ($\pm$3.8) | 277.6 ($\pm$34.2) | 667.9 ($\pm$47.0) | 585.0 ($\pm$39.6) |
| Induced Iron (Treated-Control) | — | 212.4 | 602.7 | 519.8 |

Figure 4:
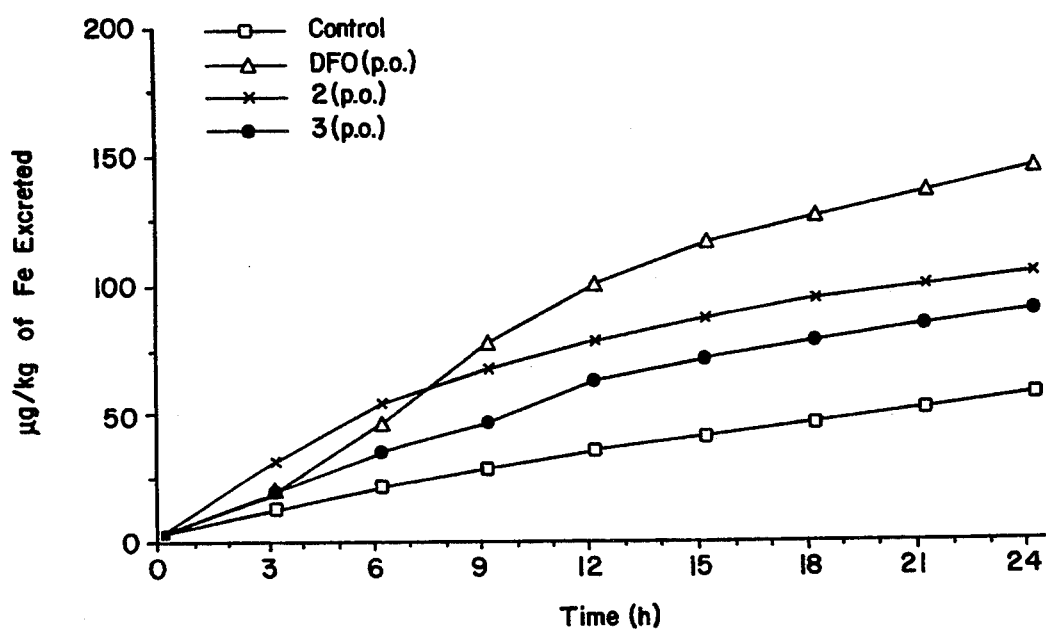
FIG. 4 is a graphical depiction of the cumulative biliary iron clearance induced by analogs (2) and (3) compared with that of DFO (1) when administered orally.

Polyether DFO analog (2), when administered orally at 150 $\mu$mol/kg to fasted rats, was 0.50 times as effective as DFO administered orally at the same dose. Bis(-triether) analog (3), also given orally to fasted rats, was 0.40 times as effective as DFO (p.o.) and 0.S0 times as effective as the chelator (2) (FIG. 4). Urinary iron clearonce bile flow was established. the cannula was tied snugly in place. A skin tunneling needle was inserted from the shoulder area around to the abdominal incision. The cannula was threaded through the needle until it emerged from the shoulder opening.

The cannula was passed from the rat to the swivel inside a metal torque-transmitting tether which was attached to a rodent jacket around the animal's chest. The cannula was directed from the rat to a Gilson micro fraction collector by a fluid swivel mounted above the metabolic cage. This system allowed the animal to move freely in the cage while continuous bile samples were being collected. Urine samples were taken every 24 hours.

EXAMPLE 2

N-(tert-Butoxycarbonyl)-N-(4-cyanobutyl)-O-benzylhydroxylamine (4) was synthesized by adding sodium iodide (84 mg, 0.56 mmol) and then sodium hydride (80% oil dispersion, 0.49 g, 16.3 mmol) to O-benzyl-N-tert-butoxycarbonyl hydroxylamine (2.68 g, 12.0 mmol) in dry DMF (40 ml). After stirring for 15 minutes, 5-chlorovaleronitrile (1.5 mL, 13.3 mmol) was added and the suspension heated at 80°–85° C. for 4 hours under argon. After cooling, the reaction was quenched with $H_2O$ (100 mL), then extracted with ether (4×75 mL). The combined organic layers were washed with 100 mL each of 1% aqueous $Na_2SO_3$, $H_2O$ and brine and then concentrated to give 4.39 g crude product. Column chromatography with 4.5% EtOAc/$CHCl_3$ produced 3.17 g of O-benzyl-N-(tert-butoxycarbonyl)-N-(4-cyanobutyl)hydroxylamine (4) (87% yield): NMR δ 1.5–1.75 (s+m, 13 H), 2.3 (t, 2 H), 3.4 (t, 2 H), 4.77 (s, 2 H), 7.3 (s, 5 H). Anal. calcd. for $C_{17}H_{24}N_2O_3$: C, 67.08; H, 7.95; N, 9.20. Found: C, 67.19; H, 7.99; N, 9.11.

EXAMPLE 3

N-(4-Cyanobutyl)-O-benzylhydroxylamine (5) was synthesized by adding trifluoroacetic acid (TFA, 16 mL) to (4) (2.59 g, 8.51 mmol), and the solution was stirred at room temperature for 20 minutes (Drierite tube). Excess TFA was removed by rotary evaporation, saturated $NaHCO_3$ (50 mL) was added and the product was extracted into ether (3×50 mL). After a brine wash (50 mL), the organic extracts were concentrated to yield 1.77 g crude product. Column chromatography with 3% EtOH/$CHCl_3$ furnished 1.31 g of (5) (75% yield): NMR δ 1.5–1.7 (m, 4 H), 2.16–2.35 (m, 2 H), 2.78–2.98 (m, 2 H), 4.66 (s, 2 H), 5.45 (br s, 1 H), 7.28 (s, 5 H). Anal. calcd. for $C_{12}H_{16}N_2O$: C, 70.56; H, 7.90. Found: C, 70.51; H, 7.91.

EXAMPLE 4

N-Benzyloxy-N-(4-cyanobutyl) succinamic acia (6) was synthesized by charging a flask with 2.8 g (13.7 mmol) of (5) in 23 mL of pyridine and 2.1 g (20.8 mmol) of succinic arthydride, heated at 100° C. for 1.5 hours and then allowed to cool to room temperature and to stir overnight. The pyridine was removed under vacuum and the residue was dissolved in a minimal amount of chloroform and filtered. The chloroform was removed and the residue was dissolved in ether, which was extracted three times with 20% potassium bicarbonate (3×50 mL). The aqueous solutions were combined, acidified and extracted with ether. This solution was dried over anhydrous sodium sulfate, filtered and evaporated. The residue was then chromatographed on 70–230 mesh silica gel by eluting with 5% methanol in chloroform to give 4.12 g (98%) of (6): NMR δ 1.56–1.7 (m, 2 H), 1.7–1.97 (m, 2 H), 2.36 (t, 2 H), 2.60–2.80 (m, 4 H), 3.68 (t, 2 H), 4.85 (s, 2 H), 7.4 (s, 5 H); IR ($CHCl_3$) 3670, 2930, 2240, 1710, 1650, 1415, 1200 $cm^{-1}$. Anal. calcd. for $C_{16}H_{20}N_2O_4$: C, 63.17; H, 6.64. Found: C, 63.36; H, 6.74. A sample of (6) was crystallized from hexane/EtoAc, mp 71° C.

EXAMPLE 5

N-(5-Aminopentyl)-N-(tert-butoxycarbonyl)-O-benzylhydroxylamine (7) was prepared by adding Raney nickel (W-2 grade, 0.98 g) and concentrated $NH_4OH$ (1.6 mL) to a solution of (4) (0.57 g, 1.87 mmol) in methanol (9.5 mL) in a 250 mL Parr bottle. The suspension was cooled to 0° C. and ammonia was gently bubbled in for 10 minutes. Hydrogenation was carried out on a Parr shaker for 3.5 hours at 55–58 psi. The catalyst was filtered off (Celite) and the filtrate was concentrated to give 0.61 g crude product. Column chromatography using 5% concentrated $NH_4OH$/$CH_3OH$ yielded 0.48 g of (7) (83% yield): NMR δ 1.25–1.72 (m, 17 H), 2.64 (t, 2 H, J=7), 3.39 (t, 2 H, J=7), 4.78 (s, 2 H), 7.31 (s, 5 H). Anal. calcd. for $C_{17}H_{28}N_2O_3$: C, 66.21; H, 9.15; N, 9.08. Found: C, 66.24, H, 9.18; N, 9.05.

EXAMPLE 6

17-(tert-Butoxycarbonyl)-6,17-bis(benzyloxy)-7,10-dioxo-6,11,17-triazaheptadecanenitrile (8) was synthesized by dissolving acid (6) (3.1 g, 10.2 mmol) and amine (7) 3.4 g, 11.0 mmol) in distilled DMF (50 mL) and cooling the solution to 0° C. under $N_2$. Diphenylphosphoryl azide (3.1 g, 11.3 mmol) and triethylamine (2.2 g, 22 mmol) were added, and the solution was stirred in the cold bath for 5 hours and at room temperature for 12 hours. Solvent was removed in vacuo followed by a $CHCl_3$ work-up and column chromatography on silica gel, eluting with 5% $CH_3OH$/$CHCl_3$ to give 6.00 g (99%) of (8): NMR δ 1.18–1.88 (m, 19 H), 2.19–2.52 (m, 4 H), 2.77 (t, 2 H, J=7), 3.01–3.72 (m, 6 H), 4.78 and 4.82 (2 s, 4 H), 5.84 (br s, 1 H), 7.2–7.4(m, 10 H). A sample of (8) (38 mg) was subjected to preparative layer chromatography (4% EtOH/$CHCl_3$) to give an analytical sample of (8) (28 mg). Anal. calcd. for $C_{33}H_{46}N_4O_6$: C, 66.64; H, 7.80; N, 9.42. Found: C, 66.48; H, 7.88; N, 9.39 [Bergeron et al, *Tetrahedron* (1989), supra].

EXAMPLE 7

6,17-Bis(benzyloxy)-7,10-dioxo-6,11,17-triazaheptadecane-nitrile (9) was synthesized by slowly adding trifluoroacetio acid (TFA, 40 mL) to (8) (6.00 g, 10.1 mmol) in $CH_2Cl_2$ (100 mL). The solution was stirred at 0° C. for 15 minutes and at room temperature for 30 minutes. Solvents were removed by rotary evaporation, aqueous $NaHCO_3$ was added and the product was extracted into $CHCl_3$. Column chromatography on silica gel, eluting with 5% $CH_3OH$/$CHCl_3$, afforded 4.3 g (87%) of (9): NMR δ 1.2–1.8 (m, 10 H), 2.2–3.3 (mr 10 H), 3.62 (t, 2 H, J=7), 4.63 (s, 2 H), 4.82 (s, 2 H), 5.5 (br s, 1 H), 5.87 (br s, 1 H), 7.15–7.35 (m, 10 H). Anal. calcd. for $C_{28}H_{38}N_4O_4$: C, 67.99; H, 7.74; N, 11.33. Found: C, 67.82; H, 7.79; N, 11.29 [Bergeron et al, Tetrahedron (1989), supra].

EXAMPLE 8

5,16-Bis(benzyloxy)-20-cyano-4,12,15-trioxo-5,11,16-triazaeicosanoic acid (10 ) was prepared by heating a solution of (9) (0.365 g, 0.738 mmol) and succinic anhydride (0.113 g, 1.13 mmol) in pyridine (10 mL) at 106° C. for 1.5 hours under $N_2$. After removing the pyridine in vacuo, the residue was diluted with ether (25 mL) and then extracted with saturated $NaHCO_3$ (3×25 mL). The combined aqueous portion was extracted further with ether (2×25 mL), then cautiously acidified with cold 6 N HCl (20 mL). Extraction with $CHCl_3$ (3×40 mL), followed by a final water wash (40 mL) and solvent removal led to 0.424 g of (10) (96% yield): NMR δ 1.25–1.84 (m, 10 H), 2.2–2.92 (m, 10 H), 3.05–3.33 (m, 2 H), 3.5–3.8 (m, 4 H), 4.80 and 4.83 (2 s, 4 H), 6.6 (br s, 1 H), 7.34 (s, 10 H). Anal. calcd. for $C_{32}H_{42}N_4O_7$: C, 64.63; H, 7.12; N, 9.42. Found: C, 64.70; H, 7.16; N, 9.39.

EXAMPLE 9

28-(tert-Butoxycarbonyl)-6,17,28-tris(benzyloxy)-7,10,18,21-tetraoxo-6,11,17-22,28-pentaazaoctacosanenitrile (11) was prepared by coupling acid (10) (3.8 g, 6.4 mmol) and amine (7) (2.2 g, 7.1 mmol) using diphenylphosphoryl azide by the method of (8) to give, after column chromatography (5% $CH_3OH/CHCl_3$), 5.4 g (95%) of (11): NMR δ 1.1–1.8 (s+m, 25 H), 2.13–2.85 (m, 10 H), 2.95–3.71 (m, 10 H), 4.76 and 4.80 (2 s, 6 H), 6.15 (br s, 2 H), 7.32 (s, 15 H). Anal. calcd. for $C_{49}H_{68}N_6O_9$: C 66.49; H, 7.74; N, 9.50. Found: C, 6.44; H, 7.75; N. 9.49 [Bergeron et al, "The Total Synthesis of Desferrioxamines E and G," Tetrahedron, Vol. 46, pp. 5881–5888 (1990)].

EXAMPLE 10

6,17,28-Tris (benzyloxy)-7,10,18,21-tetraoxo-6,11,17,22,28-pentaazaoctacosanenitrile (12 ) was synthesized by adding a solution of (11) (2.70 g, 3.05 mmol) in $CH_2Cl_2$ (50 mL) over 9 minutes to trifluoroacetic acid (18 mL) at 0° C. After stirring for 3 minutes, the ice bath was removed and stirring continued for 17 minutes. Solvents were removed by rotary evaporation, and saturated $NaHCO_3$ (200 mL) was added. Product was extracted into $CHCl_3$ (3×100 mL), and the combined organic layer washed with water (100 mL) and concentrated to give 2.46 g of (12) as an oil (quantitative). NMR δ 1.1–1.8 (m, 16 H), 2.18–3.28 (m, 16 H), 3.58 (t, 4 H), 4.63 (s, 2 H), 4.80 (s, 4 H), 7.2–7.4 (m, 15 H). Anal. calcd. for $C_{44}H_{60}N_6O_7$: C, 67.32; H, 7.70; N, 10.71. Found: C, 67.26; H, 7.74; N, 10.68.

EXAMPLE 11

6,17,28-Tris (benzyloxy)-7,10,18,21,29-pentaoxo-6,11,17,22,28-pentaazatriacontanenitrile (13 ) was prepared by dissolving compound (12) (1.1 g, 1.4 mmol) in pyridine (16 ) mL), adding acetic anhydride (4 mL) and stirring the solution for 12 hours. After removal of solvents under high vacuum, water was added, followed by extraction with $CHCl_3$. The organic extracts were washed with 1 N HCl and saturated $NaHCO_3$. Column chromatography (5% $CH_3OH/CHCl_3$) gave 1.05 g (91%) of (13): NMR δ 1.4–1.59 (m, 4 H), 1.59–1.70 (m, 6 H), 1.70–1.85 (m, 6 H), 2.1 (s, 3 H), 2.35 (t, 2 H), 2.40–2.55 (m, 4 H), 2.75–2.90 (m, 4 H), 3.18–3.28 (m, 4 H), 3.6–3.7 (m, 6 H), 4.8 (s, 2 H), 4.82 (s, 2 H), 4.84 (s, 2 H), 6.20–6.75 (m, 2 H), 7.4 (s, 15 H) . Anal. calcd. for $C_{46}H_{62}N_6O_8$: C, 66.30; H, 7.68. Found: C, 66.44; H, 7.66 [Bergeron et al, J. Org. Chem., supra].

EXAMPLE 12

Desferrioxamine B hydrochloride (I) was generated by reducing compound (13) (0.165 g, 0.2 mmol) with 68 mL of methanol, 2.7 mL of 0.1 N hydrochloric acid and 0.27 g of 10% palladium on carbon. The hydrogenation was carried out at 1 atm of hydrogen for 7.5 hours. The solution was filtered, the solvents were removed and the residue was washed. with cold methanol and then chloroform to give 0.1 g (84%) of (I). This material had a melting point of 167–168° C. and was identical to an authentic sample by 300 MHz NMR. Anat. calcd. for $C_{25}H_{49}O_8N_6Cl$: C, 50.28; H, 8.27. Found: C, 0.13, H, 8.34.

EXAMPLE 13

N-(tert-Butoxycarbonyl)-N-(3,6,9-trioxadecyl)-O-benzylhydroxylamine (14 ) was synthesized by adding sodium hydride (80% oil dispersion, 0.488 g, 16.3 mmol) to N-(tert-butoxycarbonyl)-O-benzylhydroxylamine [Ramasamy, supra] (2.66 g, 11.9 mmol) in dry DMF (20 mL), and stirring was continued for several minutes. 3,6,9-Trioxadecyl tosylate [Schultz et al, supra] (4.93 g, 15.5 mmol) in DMF (3 mL) was added by syringe, and the suspension was heated at 72° C. for 18 hours under nitrogen. After cooling, the reaction was quenched with water (100 mL) and then extracted with ether (4×50 mL). The combined organic layers were washed with brine (100 mL) and the solvent was removed in vacuo. Column chromatography with 4% $EtOH/CHCl_3$ produced 3.40 g (77%) of (14) as a liquid: NMR δ 1.50 (s, 9 H), 3.31 (s, 3 H), 3.5–3.7 (m, 12 H), 4.82 (s, 2 H), 7.25–7.41 (m, 5 H), Analysis: ($C_{19}H_{31}NO_6$) C, H, N.

EXAMPLE 14

N-(3,6,9-Trioxadecyl)-O-benzylhydroxylamine (15) was prepared by treating compound (14) (3.37 g, 9.12 mmol) with excess TFA in $CH_2Cl_2$ and worked up by the method of (9) to generate 2.24 g (91%) of (15) as a liquid: NMR δ 3.07 (t, 2 H, J=5), 3.34 (s, 3 H), 3.43–3.67 (m, 10 H), 4.67 (s, 2 H), 7.2–7.4 (m, 5 H). Analysis: ($C_{14}H_{23}NO_4$) C, H, N.

EXAMPLE 15

N-(Benzyloxy)-N-(3,6,9-trioxadecyl) succinamio acid (16) was produced by heating a solution of (15) (2.20 g, 8.17 mmol) and succinic anhydride (1.29 g, 12.9 mmol) in pyridine (26 mL) at 90° C. for 2 hours under argon. After removal of the pyridine in vacuo, the residue was combined with ether (50 mL), followed by extraction with saturated aqueous $NaHCO_3$ (2×75 mL). The aqueous portion was extracted further with ether (2×50 mL), cooled to 0° C. and cautiously acidified with cold 6 N HCl (50 mL) and then extracted with $CHCl_3$ (4×75 mL). The $CHCl_3$ layer was washed with $H_2O$ (50 mL), and solvent was removed by rotary evaporation. Column chromatography on silica gel (12% $CH_3OH/CHCl_3$) gave 2.79 g (92%) of (16) as an oil: NMR δ 2.52–2.73 (m, 4 H), 3.30 (s, 3 H), 3.4–3.8 (m, 12 H), 4.87 (s, 2 H), 6.53 (br s, 1 H), 7.33 (s, 5 H). Analysis: ($C_{18}H_{27}NO_7$) C, H, N.

EXAMPLE 16

22-(tert-Butoxycarbonyl)-11,22-bis(benzyloxy)-12,15-dioxo-11,16,22-triaza-2,5,8-trioxadocosane (17) was produced by coupling acid (16) (11.0 g, 29.8 mmol) and amine) (7) (9.2 g, 29.9 mmol) by using diphenylphosphoryl azide and the method of (8) to give 18.6 g (94%) of (17) as an oil=NMR δ 1.28–1.70 (m+s, 15 H), 2.42 (t, 2 H, J=7), 3.02–3.87 (m+st 21 H), 4.78 (st 2 H)#4.89 (st 2 H), 6.0 (br s, 1 H), 7.25–7.44 (m, 10 H). Analysis: ($C_{35}H_{53}N_3O_9$) C, H, N.

EXAMPLE 17

11,22-Bis (benzyloxy)-12,15-dioxo-11,16,22-triaza-2,5,8-trioxadocosane (18) was prepared by adding excess TFA to (17) (16.0 g, 24.2 mmol) in $CH_2Cl_2$ at 0° C. and stirring the solution at room temperature. A workup by the method of (9) gave 12.0 g (87%) of (18) as an oil: NMR δ 1.24–1.62 (m, 6 H), 2.42 (t, 2 H, J=7), 2.61–3.89 (m+s, 22 H) t 4.66 (s, 2 H), 4.87 (s, 2 H), 6.0 (br s, 1 H), 7.2–7.4 (m, 10 H). Analysis: ($C_{30}H_{45}N_3O_7$) C, H, N.

EXAMPLE 18

5,16-Bis (benzyloxy)-4,12,15-trioxo-5,11,16-triaza-19,22,25-trioxahexacosanoic acid (19) was synthesized by reacting compound (18) (3.40 g, 6.07 mmol) with succinic anhydride in pyridine following the procedure of (16) to produce 3.81 g (95%) of (19) as an oil: NMR δ 1.2–1.8 (m, 6 H) t 2.38–2.91 (m, 8 H) t 3.07–3.83 (m, 19 H) t 4.79 (s, 2 H), 4.88 (s, 2 H), 5.7 (br s, 1 H), 6.62 (br s, 1 H), 7.33 (s, 10 H). Analysis: ($C_{34}H_{49}N_3O_{10}$) C, H, N.

EXAMPLE 19

33-(tert-Butoxycarbonyl)-11,22,33-tris(benzyloxy)-2,15,23,26-tetraoxo-11,16,22,27,33-pentaaza-2,5,8-trioxatritriacontane (20) was produced by coupling acid (19) (3.78 g, 5.73 μmol) and amine (7) (2.03 g, 6.58 mmol) using diphenylphosphoryl azide by the method of (8) to give 4.22 g (78%) of (20) as a waxy solid: NMR δ 1.2–1.7 (m+s, 21 H), 2.32–2.56 (m, 4 H), 2.67–2.93 (m, 4 H), 3.05–3.88 (m, 23 H), 4.78 (s, 2 H), 4.82 (s, 2 H), 4.88 (s, 2 H), 6.23 (br s, 2 H), 7.33 (s, 15 H). Analysis: ($C_{51}H_{75}N_5O_{12}$) C, H, N.

EXAMPLE 20

11,22,33-Tris(benzyloxy)-12,15,23,26-tetraoxo-11,16,22,27,33-pentaaza-2,5,8-trioxatritriacontane (21) was prepared by adding excess TFA to (20) (2.05 g, 2.16 mmol) in $CH_2Cl_2$ at 0° C. The solution was stirred at room temperature and worked up by the method of (9) to give 1.91 g (quantitative) of (21) as a waxy solid: NMR δ 1.18–1.70 (m, 12 H), 2.32–3.33 (m, 18 H), 3.39–3.80 (m, 14 H), 4.64 (s, 2 H), 4.80 (s, 2 H), 4.87 (s, 2 H), 6.23 (br s, 2 H), 7.2–7.4 (m, 15 H). Analysis: ($C_{46}H_{67}N_5O_{10}\cdot H_2O$) C, H, N.

EXAMPLE 21

11,22,33-Tris(benzyloxy)-12,15,23,26,34-pentaoxo-11,16,22,27,33-pentaaza-2,5,8-trioxapentatriacontane (22) was produced by treating compound (21) (1.1 g, 1.29 mmol) with acetic arthydride in pyridine by the method of (13) to afford 1.05 g (91%) of (22) as a waxy solid: NMR δ 1.13–1.77 (m, 2 H), 2.06 (s, 3 H), 2.3–2.9 (m, 8 H), 2.99–3.34 (m+s, 7 H), 3.48–3.77 (m, 16 H), 4.75 (s, 2 H), 4.80 (s, 2 H), 4.87 (s, 2 H), 6.2 (br s, 2 H), 7.33 (s, 15 H). Analysis: ($C_{48}H_{69}N_5O_{11}$) C, H, N.

EXAMPLE 22

11,22,33-Tris(benzyloxy)-12,15,23,26,34-pentaoxo-11,16,22,27,33-pentaaza-2,5,8,36,39,42-hexaoxatritetracontane (23) was synthesized by reacting compound (21) (3.91 g, 4.60 mmol) with 3,6,9-trioxadecanoyl chloride [Helmann, supra] ($NEt_3/CH_2Cl_2$) to give 4.0 g (78%) of (23): NMR δ 1.17–1.78 (m, 12 H), 2.3–2.9 (m, 8 H), 3.04–3.37 (m, 10 H), 3.4–3.8 (m, 24 H), 4.21 (s, 2 H), 4.76 (s, 2 H), 4.81 (s, 2 H), 4.88 (s, 2 H), 6.17–6.37 (m, 2 H), 7.34 (s, 15 H). Analysis: ($C_{53}H_{79}N_5O_{14}$) C, H, N.

EXAMPLE 23

11,22,33-Trihydroxy-12,15,23,26,34-pentaoxo-11,16,22,27,33-pentaaza-2,5,8-trioxapentatriacontane (2) was prepared by dissolving compound (22) (2.6 g, 2.92 mmol) in distilled $CH_3OH$ (200 mL) in acid-washed glassware, and 10% Pd-C (1.1 g) was introduced. The mixture was stirred under a hydrogen atmosphere for 2 hours, solids were filtered using analytical grade Celite and the filtrate was concentrated to furnish 1.56 g (86%) of (2) as an amorphous white solid: NMR ($D_2O$) δ 1.17–1.80 (m, 12 H), 2.11 (s, 3 H), 2.33–2.93 (m, 8 H), 3.15 (t, 4 H, J=7), 3.33 (s, 3 H), 3.46–3.84 (m, 16 H). Analysis: ($C_{27}H_{51}N_5O_{11}$) C, H, N.

EXAMPLE 24

11,22,33 -Trihydroxy-12,15,23,26,34-pentaoxo-11,16,22,27,33-pentaaza-2,5,8,36,39,42-hexaoxatritetracontane (3) was produced by debenzylating compound (23) (2.0 g, 1.8 mmol) by the method of (2) to furnish 1.35 g (80%) of (3) as an amorphous solid. A sample of (3) (0.845 g) was passed through Sephadex LH-20 eluting with EtOH to afford an analytical sample (0.766 g) of (3): NMR ($D_2O$) δ 1.10–1.78 (m, 12 H), 2.33–2.93 (m, 8 H), 3.15 (t, 4 H, J=7), 3.33 (s, 6 H), 3.47–3.85 (m, 24 H), 4.38 (s, 2 H). Analysis: ($C_{32}H_{61}N_5O_{14}$) C, H, N.

ANALYTICAL DATA (2) Anal. calcd. for $C_{27}H_{51}N_5O_{11}$: C, 52.16; H, 8.27; N, 11.26. Found: C, 51.89; H, 8.19; N, 11.18.

(3) Anal. calcd. for $C_{32}B_{61}N_5O_{14}$: C, 51.95; H, 8.31; N, 9.47. Found: C, 51.69; H, 8.37; N, 9.42.

(14) Anal. calcd. for $C_{19}H_{31}NO_6$: C, 61.77; H, 8.46; N, 3.79. Found: C, 61.71; H, 8.49; N, 3.76.

(15) Anal. calcd. for $C_{14}H_{23}NO_4$: C, 62.43; H, 8.61; N, 5.20. Found: C, 62.19; H, 8.64; N, 5.12.

(16) Anal. calcd. for $C_{18}H_{27}NO_7$: C, 58.52; H, 7.37; N, 3.79. Found: C, 58.35; H, 7.39; N, 3.71.

(17) Anal. calcd. for $C_{35}H_{53}N_3O_9$: C, 63.71; H, 8.10; N, 6.37. Found: C, 63.45; H, 8.04; N, 6.33.

(18) Anal. calcd. for $C_{30}H_{45}N_3O_7$: C, 64.38; H, 8.10; N, 7.51. Found: C, 64.10; H, 8.15; N, 7.47.

(19) Anal. calcd. for $C_{34}H_{49}N_3O_{10}$: C, 61.90; H, 7.48; N, 6.37. Found: C, 61.71; H, 7.47; N, 6.33.

(20) Anal. calcd. for $C_{51}H_{75}N_5O_{12}$: C, 64,47; H, 7.96; N, 7.37. Found: C, 64.26; H, 8.03; N, 7.29.

(21) Anal. calcd. for $C_{46}H_{67}N_5O_{10}\cdot H_2O$: C, 63.65; H, 8.01; N, 8.07. Found: C, 63.96; H, 7.82; N, 8.10.

(22) Anal. calcd. for $C_{48}H_{69}N_5O_{11}$: C, 64.63; H, 7.80; N, 7.85. Found: C, 64.52 ; H, 7.83; N, 7.82.

(23) Anal. calcd. for $C_{53}H_{79}N_5O_{14}$: C, 63.01; H, 7.88; N, 6.93. Found: C, 63.13 ; H, 7.921 N, 6.97.

I claim:

1. A method for synthesizing a polyether analog of desferrioxamine B or a homolog thereof having the formula:

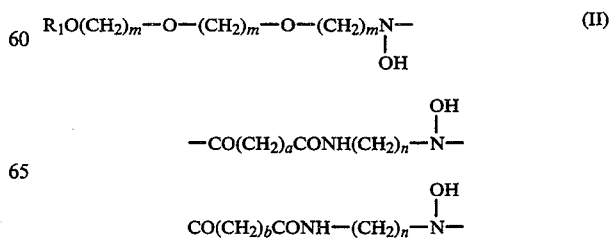

-continued
$$-CO(CH_2)_{m-1}O(CH_2)_mO(CH_2)_m-OR_2$$

wherein each
n may be the same or different and is an integer from 1 to 10,
a is an integer from 1 to 6,
b is an integer from 1 to 6,
m is an integer from 2 to 6,
$R_1$ and $R_2$ may be the same or different and are alkyl, straight or branched chain, having 1-10 carbon atoms, comprising:

(a) reacting a compound of the formula:

$$R_1O(CH_2)_mO(CH_2)_mO(CH_2)_mOACT \quad (13)$$

wherein ACT is an alcohol activating group, with a compound of the formula:

$$Q-NH-OZ$$

wherein
Q is an amino protecting group and
Z is a hydroxyl protecting group,
to produce a compound of the formula:

$$R_1O(CH_2)_mO(CH_2)_mO(CH_2)_m-\overset{OZ}{\underset{|}{N}}-Q \quad (14)$$

and cleaving Q to produce a compound of the formula:

$$R_1O(CH_2)_mO(CH_2)_mO(CH_2)_m-\overset{OZ}{\underset{|}{N}}H \quad (15)$$

(b) reacting compound (15) with an anhydride of the formula:

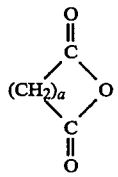

$$R_1O(CH_2)_mO(CH_2)_mO(CH_2)_m\overset{OZ}{\underset{|}{N}}-CO(CH_2)_aCOOH \quad (16)$$

(c) reacting compound (16) with a compound of the formula:

$$H_2N(CH_2)_n\overset{OZ}{\underset{|}{N}}-Q \quad (7)$$

to produce a compound of the formula:

$$R_1O(CH_2)_mO(CH_2)_mO(CH_2)_m\overset{OZ}{\underset{|}{N}}-CO(CH_2)_aCONH(CH_2)_n\overset{OZ}{\underset{|}{N}}-Q \quad (17)$$

and cleaving Q therefrom to produce a compound of the formula:

$$R_1O(CH_2)_mO(CH_2)_mO(CH_2)_m\overset{OZ}{\underset{|}{N}}CO(CH_2)_aCONH(CH_2)_n-\overset{OZ}{\underset{|}{N}}-H \quad (18)$$

(d) reacting compound (18) with an anhydride of the formula:

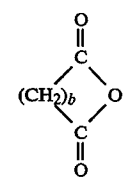

to produce a compound of the formula:

$$R_1O(CH_2)_mO(CH_2)_mO(CH_2)_m\overset{OZ}{\underset{|}{N}}CO(CH_2)_a- \quad (19)$$
$$-CONH(CH_2)_n\overset{OZ}{\underset{|}{N}}CO(CH_2)_bCOOH$$

(e) reacting compound (19) with compound (7) to produce a compound of the formula:

$$R_1O(CH_2)_mO(CH_2)_mO(CH_2)_m\overset{OZ}{\underset{|}{N}}CO(CH_2)_a- \quad (20)$$
$$-CONH(CH_2)_n\overset{OZ}{\underset{|}{N}}CO(CH_2)_bCONH(CH_2)_n\overset{OZ}{\underset{|}{N}}-Q$$

and cleaving Q therefrom to produce a compound of the formula:

$$R_1O(CH_2)_mO(CH_2)_mO(CH_2)_m\overset{OZ}{\underset{|}{N}}CO(CH_2)_a- \quad (21)$$
$$-CONH(CH_2)_n\overset{OZ}{\underset{|}{N}}CO(CH_2)_bCONH(CH_2)_n\overset{OZ}{\underset{|}{N}}-H$$

(f) reacting compound (21) with a compound of the formula:

$$R_2O(CH_2)_mO(CH_2)_mO(CH_2)_{m-1}COX \quad (22)$$

wherein X is any leaving group which renders the compound sufficiently active to acylate (21), and $R_2$ is alkyl, straight or branched chain, having 1-10 carbon atoms, to produce a compound of the formula:

$$R_1O(CH_2)_mO(CH_2)_mO(CH_2)_m\overset{OZ}{\underset{|}{N}}CO(CH_2)_aCONH(CH_2)_n\overset{OZ}{\underset{|}{N}}- \quad (23)$$
$$CO(CH_2)_bCONH(CH_2)_n\overset{OZ}{\underset{|}{N}}CO(CH_2)_{m-1}O(CH_2)_mO(CH_2\overset{}{)_m}O-R_2$$

and
(g) reducing said compound (23) to produce said compound of formula (II).

2. A method according to claim 1 wherein $R_1$ and $R_2$ are methyl and m is 2.

3. A method for synthesizing a polyether analog of desferrioxamine B or a homolog thereof having the formula:

$$R_1O(CH_2)_mO(CH_2)_mO(CH_2)_m\overset{\overset{OH}{|}}{N}CO(CH_2)_a- \quad (III)$$

$$-CONH(CH_2)_n\overset{\overset{OH}{|}}{N}CO(CH_2)_bCONH(CH_2)_n-$$

$$\overset{\overset{OH}{|}}{N}-COR_3$$

wherein
m is an integer from 2 to 6,
each n may be the same or different and is an integer from 1 to 10,
a is an integer from 1 to 6,
b is an integer from 1 to 6,
$R_1$ is alkyl, straight or branched chain, having 1–10 carbon atoms, and
$R_3$ is alkyl, straight or branched chain, having 1–14 carbon atoms, comprising:

(a) reacting a compound of the formula:

$$R_1O(CH_2)_mO(CH_2)_mO(CH_2)_mOACT \quad (1)$$

wherein ACT is an alcohol activating group, with a compound of the formula:

$$Q-NH-OZ$$

wherein
Q is an amino protecting group and
Z is a hydroxyl protecting group, to produce a compound of the formula:

$$R_1O(CH_2)_mO(CH_2)_mO(CH_2)_m\overset{\overset{OZ}{|}}{N}-Q \quad (14)$$

and cleaving Q therefrom to produce a compound of the formula:

$$R_1O(CH_2)_mO(CH_2)_mO(CH_2)_m\overset{\overset{OZ}{|}}{N}H \quad (15)$$

(b) reacting compound (15) with an anhydride of the formula:

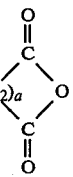

to produce a compound of the formula:

$$R_1O(CH_2)_mO(CH_2)_mO(CH_2)_m\overset{\overset{OZ}{|}}{N}CO(CH_2)_aCOOH \quad (16)$$

(c) reacting compound (16) with a compound of the formula:

$$H_2N(CH_2)_n\overset{\overset{OZ}{|}}{N}-Q \quad (7)$$

to produce a compound of the formula:

$$R_1O(CH_2)_mO(CH_2)_mO(CH_2)_m\overset{\overset{OZ}{|}}{N}CO(CH_2)_aCONH(CH_2)_n-\overset{\overset{OZ}{|}}{N}-Q \quad (17)$$

and cleaving Q therefrom to produce a compound of the formula:

$$R_1O(CH_2)_mO(CH_2)_mO(CH_2)_m\overset{\overset{OZ}{|}}{N}CO(CH_2)_aCONH(CH_2)_n-\overset{\overset{OZ}{|}}{N}-H \quad (18)$$

(d) reacting compound (18) with an anhydride of the formula:

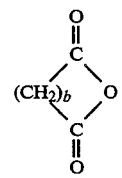

to produce a compound of the formula:

$$R_1O(CH_2)_mO(CH_2)_mO(CH_2)_m\overset{\overset{OZ}{|}}{N}CO(CH_2)_aCONH(CH_2)_n\overset{\overset{OZ}{|}}{N}CO(CH_2)_bCOOH \quad (19)$$

(e) reacting compound (19) with compound (7) to produce a compound of the formula:

$$R_1O(CH_2)_mO(CH_2)_mO(CH_2)_m\overset{\overset{OZ}{|}}{N}CO(CH_2)_aCONH(CH_2)_n\overset{\overset{OZ}{|}}{N}CO(CH_2)_bCONH(CH_2)_n\overset{\overset{OZ}{|}}{N}-Q \quad (20)$$

and cleaving Q therefrom to produce a compound of the formula:

$$R_1O(CH_2)_mO(CH_2)_mO(CH_2)_m\overset{\overset{OZ}{|}}{N}CO(CH_2)_aCONH(CH_2)_n\overset{\overset{OZ}{|}}{N}CO(CH_2)_bCONH(CH_2)_n\overset{\overset{OZ}{|}}{N}-H \quad (21)$$

(f) reacting compound (21) with an anhydride of the formula:

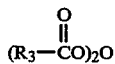

or an activated ester or acyl halide of the formula:

wherein $R_3$ is as defined above and X is any leaving group sufficiently active to acylate (21), to produce a compound of the formula:

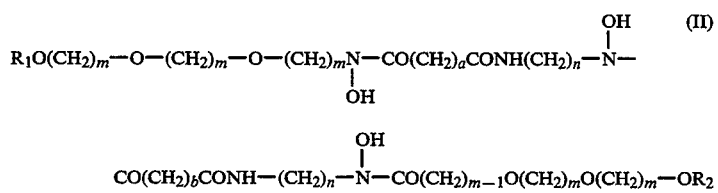

and (g) reducing said compound (22) to produce said compound (III).

4. A method according to claim 3 wherein $R_3$ is methyl and m is 2.

5. A compound of the formula:

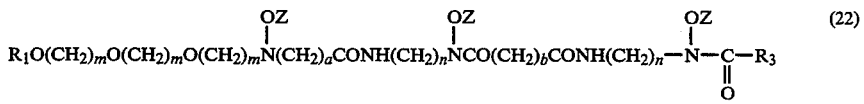

wherein
- m is an integer from 2 to 6,
- each n may be the same or different and is an integer from 1 to 10,
- a is an integer from 1 to 6,
- b is an integer from 1 to 6,
- $R_1$ is alkyl, straight or branched chain, having 1–10 carbon atoms, and
- $R_3$ is alkyl, straight or branched chain, having 1–14 carbon atoms.

6. A compound of the formula:

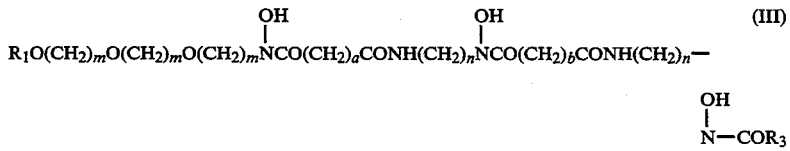

wherein each
- n may be the same or different and is an integer from 1 to 10,
- a is an integer from 1 to 6,
- b is an integer from 1 to 6,
- m is an integer from 2 to 6,
- $R_1$ and $R_2$ may be the same or different and are alkyl, straight or branched chain, having 1–10 carbon atoms.

* * * * *

UNITED STATES PATENT AND TRADEMARK OFFICE
CERTIFICATE OF CORRECTION

PATENT NO. : 5,367,113

DATED : November 22, 1994

INVENTOR(S) : Raymond J. BERGERON, JR.

PAGE 1 OF 4

It is certified that error appears in the above-identified patent and that said Letters Patent is hereby corrected as shown below:

On the title page in column 2, line 7 under "[57] Abstract" change "vide" to -- provide --

Column 1, line 12: after "1993" insert -- ) --

Column 1, line 34: change "re" to -- Fe --

Column 4, line 27: change "hydrocathyl" to -- hydrocarbyl --

Column 5, line 50: between formulae (16) and (7) insert -- (c) reacting compound (16) with a compound of the formula: --

Column 7, line 20: change "Q-NEOZ" to -- Q-NHOZ --

Column 9, line 40: change "Bergeton" to -- Bergeron --

Column 9, line 57: change "Bergeton" to -- Bergeron --

Column 10, line 46: change "polyethercon-" to -- polyether con- --

Column 11, line 4: change "Nail" to -- NaH --

UNITED STATES PATENT AND TRADEMARK OFFICE
CERTIFICATE OF CORRECTION

PATENT NO. : 5,367,113
DATED : November 22, 1994
INVENTOR(S) : Raymond J. BERGERON, JR.                PAGE 2 OF 4

It is certified that error appears in the above-identified patent and that said Letters Patent is hereby corrected as shown below:

Column 11, line 14: change "Bergeton" to -- Bergeron --

Column 11, line 29: change "Bergeton" to -- Bergeron --

Column 11, line 65: change "Bergeton" to -- Bergeron --

Column 12, line 9: change "Bergeton" to -- Bergeron --

Column 12, lines 18-19: change "Bergeton" to -- Bergeron --

Column 12, line 36: change "butoxycarbonyl)-O-benzyihydroxylamine" to -- butoxycarbonyl)-O-benzylhydroxylamine --

Column 12, line 38: change "Bergeton" to -- Bergeron --

Column 12, line 54: change "lationamine" to -- lation. Amine --

Column 13, line 67: change "0.S0" to -- 0.80 --

Column 14, line 65: change "(j.p.)" to -- (i.p.) --

UNITED STATES PATENT AND TRADEMARK OFFICE
CERTIFICATE OF CORRECTION

PATENT NO. : 5,367,113
DATED : November 22, 1994
INVENTOR(S) : Raymond J. BERGERON, JR.     PAGE 3 OF 4

It is certified that error appears in the above-identified patent and that said Letters Patent is hereby corrected as shown below:

Column 15, line 55: change "acia" to -- acid --

Column 15, line 58: change "arthydride" to -- anhydride --

Column 16, line 51: change "trifluoroacetio" to -- trifluoroacetic --

Column 18, line 4: change "washed." to -- washed --

Column 18, line 7: change "Anat." to -- Anal. --

Column 18, line 41: change "succinamio" to -- succinamic --

Column 18, line 65: change "=" to -- : --

Column 18, line 66: change "(m + st 21 H), 4.78 (st 2 H)#4.89" to -- (m + s, 21 H), 4.78 (s, 2 H), 4.89 --

Column 18, line 67: change "(st 2 H)" to -- (s, 2 H) --

Column 19, line 9: change "(m + s, 22 H) t 4.66" to -- (m + s, 22 H), 4.66 --

UNITED STATES PATENT AND TRADEMARK OFFICE
CERTIFICATE OF CORRECTION

PATENT NO. : 5,367,113
DATED : November 22, 1994
INVENTOR(S) : Raymond J. BERGERON, JR.

It is certified that error appears in the above-identified patent and that said Letters Patent is hereby corrected as shown below:

Column 19, line 19: change "(m, 6 H) t 2.38-2.91 (m, 8 H) t" to -- (m, 6 H), 2.38-291 (m, 8 H), --

Column 19, line 52: change "arthydride" to -- anhydride --

Column 19, line 64: change "Helmann" to -- Heimann --

Column 20, line 46: change "calcd," to -- calcd. --

Column 21, line 49: before formula (16), insert -- to produce a compound of the formula: --

Signed and Sealed this

Twenty-first Day of February, 1995

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,367,113
DATED : November 22, 1994
INVENTOR(S) : Raymond J. BERGERON, Jr.

It is certified that error appears in the above-identified patent and that said Letters Patent is hereby corrected as shown below:

Column 1, line 7: after "Grant No." change "HL-42817" to -- 5R01-HL-42817. The United States Government has certain rights in and to the invention claimed herein. --

Signed and Sealed this

Second Day of July, 1996

Attest:

*Attesting Officer*

BRUCE LEHMAN

*Commissioner of Patents and Trademarks*